United States Patent [19]

Olsson et al.

[11] 4,451,663
[45] May 29, 1984

[54] CARBAMATE INTERMEDIATES FOR BRONCHOSPASMOLYTICS

[75] Inventors: O. A. Torsten Olsson; Leif A. Svensson, both of Lund; Kjell I. L. Wetterlin, Sandby, all of Sweden

[73] Assignee: Aktiebolaget Draco, Lund, Sweden

[21] Appl. No.: 395,650

[22] Filed: Jul. 6, 1982

Related U.S. Application Data

[62] Division of Ser. No. 279,672, Jul. 1, 1981, Pat. No. 4,419,364.

[30] Foreign Application Priority Data

Jul. 9, 1980 [GB] United Kingdom ............... 8022439
May 29, 1981 [GB] United Kingdom ............... 8116441

[51] Int. Cl.³ ................ C07C 125/04; C07C 125/067
[52] U.S. Cl. ............................................ 560/29; 560/164
[58] Field of Search ................................ 560/164, 29

[56] References Cited

U.S. PATENT DOCUMENTS 3,657,319  4/1972  Kaiser et al. ............... 560/29 X
4,063,025 12/1977  Murakami et al. ......... 560/29
4,214,001  7/1980  Engelhardt et al. ........ 560/29 X

*Primary Examiner*—Bernard Helfin
*Attorney, Agent, or Firm*—Brumbaugh, Graves, Donohue & Raymond

[57] ABSTRACT

New bronchospasmolytically active compounds exhibiting long duration of action and reduced undesired side effects of the structural formula

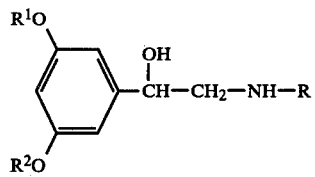

I and therapeutically acceptable salts thereof, in which formula R is selected from the group consisting of $-C(CH_3)_3$,

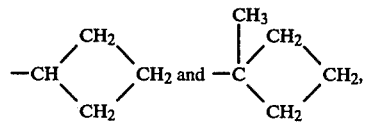

$R^1$ is selected from the group consisting of H and $R^2$,
$R^2$ represents the radical of the formula

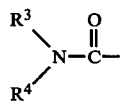

wherein
$R^3$ is selected from the group consisting of
(a) H
(b) alkyl groups containing 1–3 carbon atoms (c)

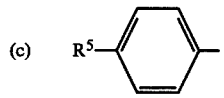

wherein
$R^5$ is selected from the group consisting of
(a) OH
(b) alkoxy groups containing 1–3 carbon atoms and
wherein
$R^4$ is selected from the group consisting of
(a) H
(b) alkyl groups containing 1–3 carbon atoms, with the proviso that $R^3$ and $R^4$ are combined as follows:

| when $R^3$ is | then $R^4$ is |
|---|---|
| H | H |
| alkyl group of 1–3 carbon atoms | H or an alkyl group of 1–3 carbon atoms |
| $R^5\text{-}\phantom{x}$ phenyl | H | processes for the preparation thereof, chemical intermediates at their preparation, pharmaceutical preparations containing them, and their medicinal use.

2 Claims, No Drawings

CARBAMATE INTERMEDIATES FOR BRONCHOSPASMOLYTICS

This is a division, of application Ser. No. 279,672, filed July 1, 1981 and now U.S. Pat. No. 4,419,364.

FIELD OF THE INVENTION

The present invention relates to novel compounds having therapeutic activity, to processes for their preparation, to chemical intermediates at their preparation, to pharmaceutical preparations containing them and to the medicinal use of the compounds. In particular, the compounds of the invention have bronchospasmolytic effect and are effective in the treatment of reversible obstructive lung ailments of various genesis, particulary asthmatic conditions. The compounds exhibit a prolonged duration of therapeutic effect and a reduced degree of side effects, especially a reduced heart-stimulating effect.

BACKGROUND OF THE INVENTION

It is desirable to find bronchodilating agents which have longer duration of activity than the substances which are available on the market. The compound known under the generic name terbutaline, of the structural formula

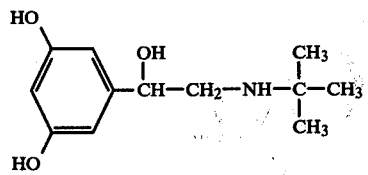

is one of the presently preferred long-acting bronchodilating drugs on the market and is described i.e. in the U.S. Pat. No. 4,011,258, has a duration of therapeutic activity of about 6 to 8 hours. This duration is confirmed by many years of clinical experience and can be quantified by the finding that a serum concentration of at least about 2 ng/ml of terbutaline is necessary for obtaining the desired therapeutic activity (Hörnblad et al., Europ J. clin Pharmacol. 10 9-18 (1976)).

Another long-acting bronchospasmolytically effective compound available on the market, salbutamol of the structural formula

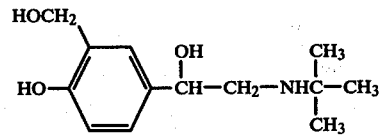

has a duration of bronchospasmolytic activity which is about equal to the duration of terbutaline.

Attempts to obtain bronchospasmolytically active compounds with long duration of activity are reported in the literature. Thus, Zölss, Sci. Pharm. 32 (1964) 2 76-92 discloses i.e. certain esters of ethanol amine derivatives known at that time. Minatoya, The Journal of Pharmacology and Experimental Therapeutics Vol. 206 No. 3, 515–527, discusses the pharmacological properties of a compound known as bitolterol of the formula

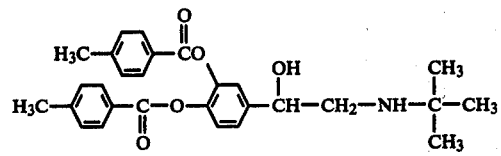

The compound bitolterol which also is disclosed in the Belgian Pat. No. 748 178 proved to have a duration of activity comparable with that of salbutamol.

The problem underlying the present invention was to find orally active bronchospasmolytic agents which have a clinically useful duration of activity of at least 12 hours.

OUTLINE OF THE INVENTION

The present invention provides new compounds having bronchospasmolytic activity at oral administration and exhibiting a duration of activity of up to 12 hours or more. The compounds of the invention also exhibit a lower degree of undesired cardiovascular side effects. Thus, they exhibit less chronotropic and inotropic effect than terbutaline.

The invention also relates to methods for preparation of the compounds, pharmaceutical composition containing the compounds as active ingredients, and to the use of the compounds for therapeutic purposes, in particular the use for producing bronchodilation in mammals including humans. Furthermore, the invention relates to the use of the compounds for producing relaxation of the human uterus, and to pharmaceutical preparations containing the compounds of the invention in combination with a conventionally used bronchodilating agent, as described more in detail below.

DETAILED DESCRIPTION OF THE INVENTION

The invention relates to new compounds of the formula

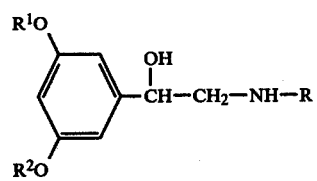

I and therapeutically acceptable salts thereof, in which formula

R is selected from the group consisting of —C(CH₃)₃,

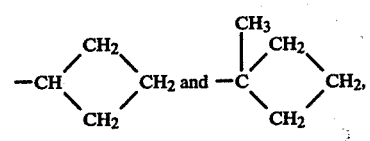

R¹ is selected from the group consisting of H and R²,
R² represents the radical of the formula

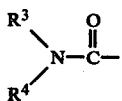

wherein
R³ is selected from the group consisting of
(a) H
(b) alkyl groups containing 1–3 carbon atoms (c) 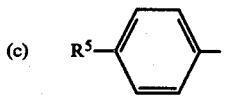

wherein
R⁵ is selected from the group consisting of
(a) OH
(b) alkoxy groups containing 1–3 carbon atoms and
wherein
R⁴ is selected from the group consisting of
(a) H
(b) alkyl groups containing 1–3 carbon atoms with the proviso that R³ and R⁴ are combined as follows:

| When R³ is | then R⁴ is |
|---|---|
| H | H |
| alkyl group of 1–3 carbon atoms | H or an alkyl group of 1–3 carbon atoms |
| 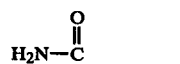 | H |

The formula I thus encompasses compounds having one hydroxy substituent in position 3 or 5 on the phenyl radical substituted and the other hydroxy substituent unsubstituted, and compounds having both of the hydroxy groups in the base structure substituted.

Illustrative examples of the radicals R¹ and R² are:

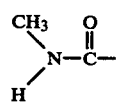

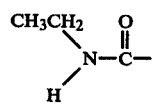

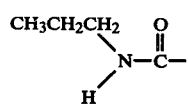

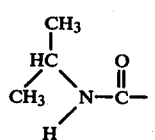

-continued

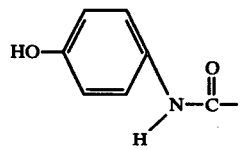

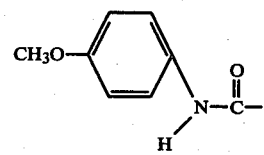

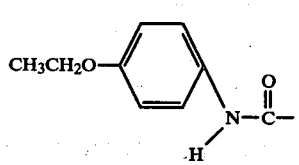

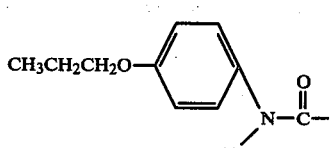

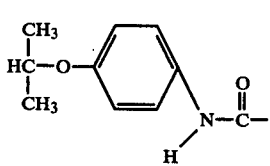

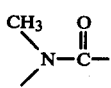

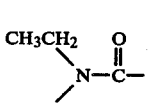

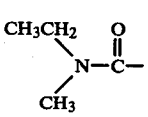

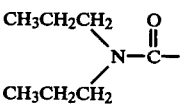

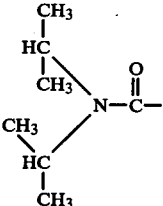

Illustrative examples of compounds of the invention are:

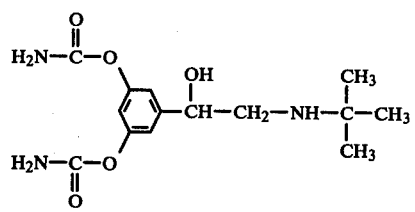
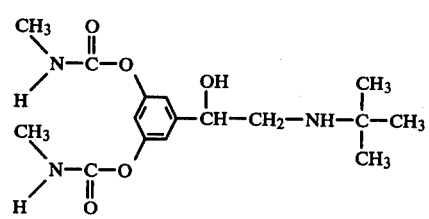
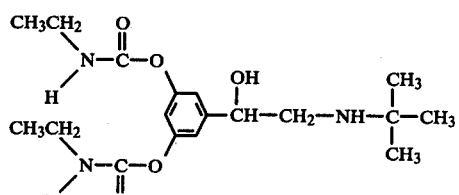
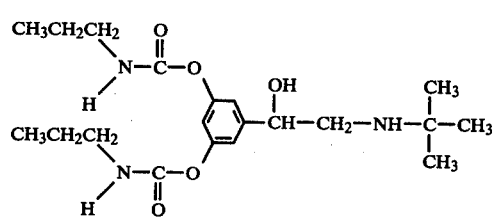
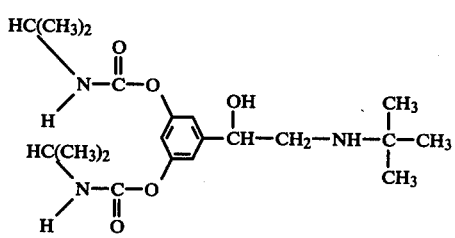
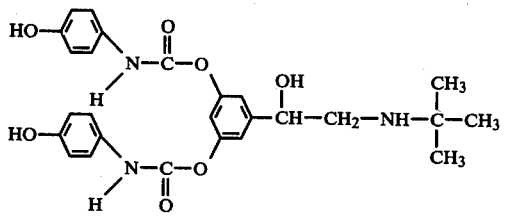
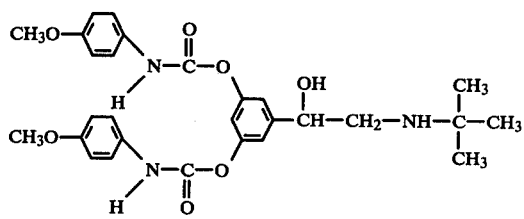
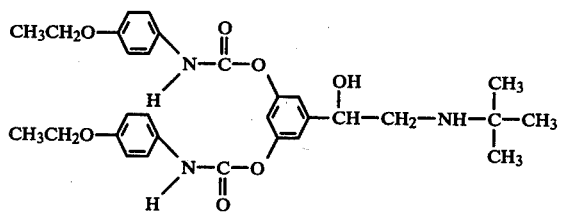
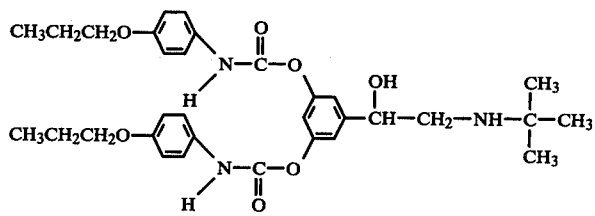
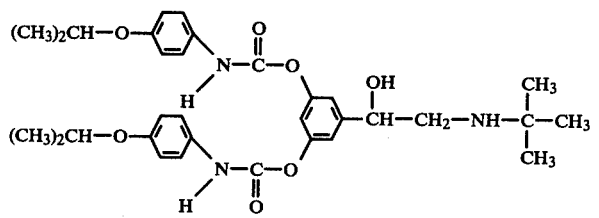
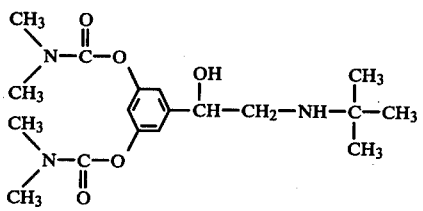

-continued
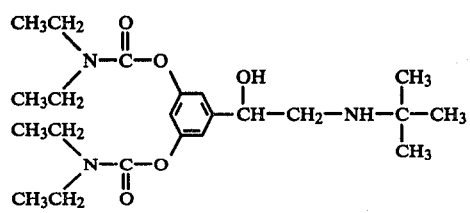
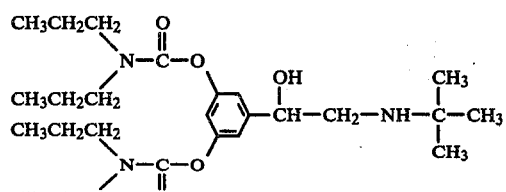
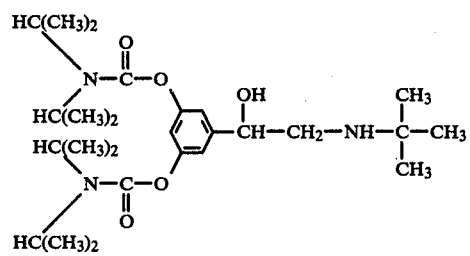
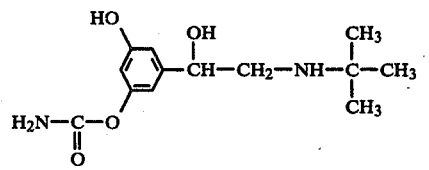
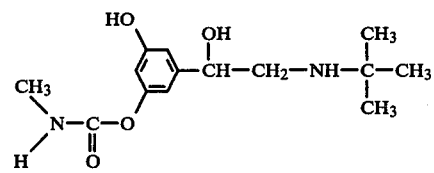
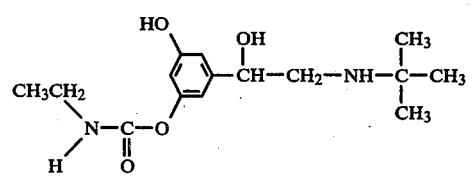
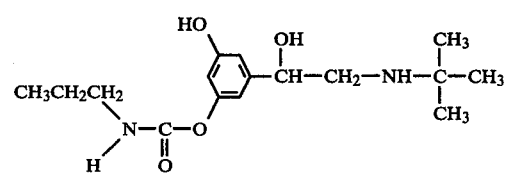
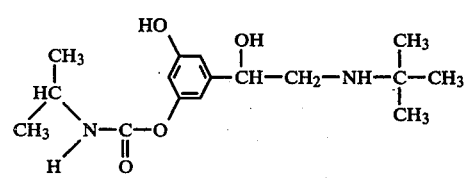
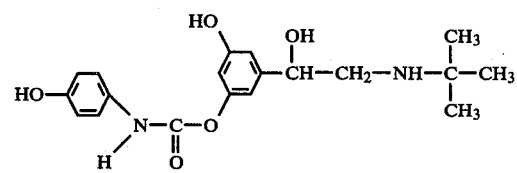
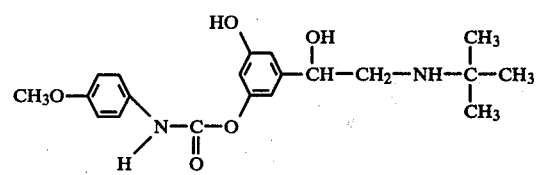
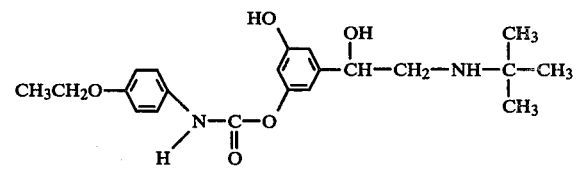
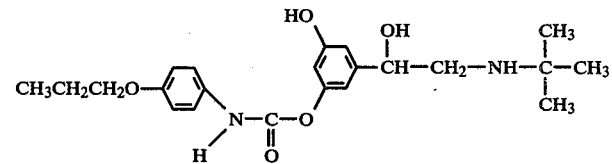
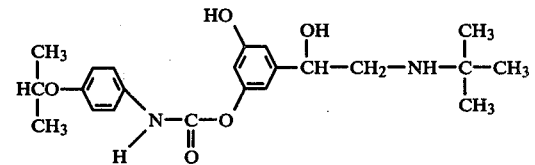
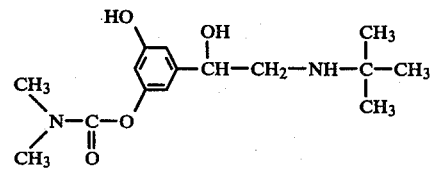

-continued
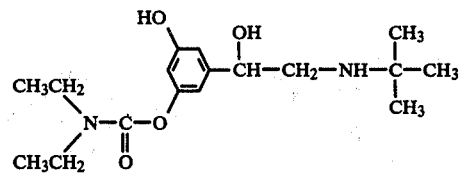
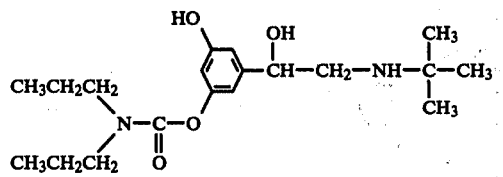
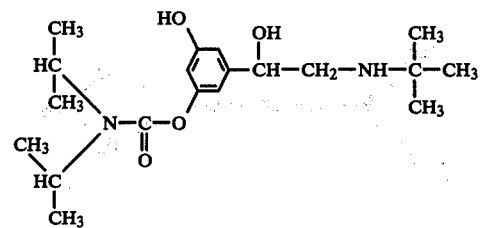
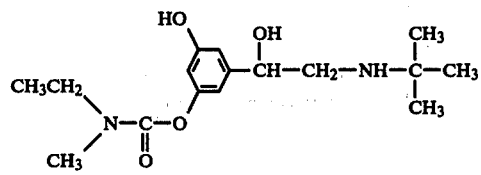
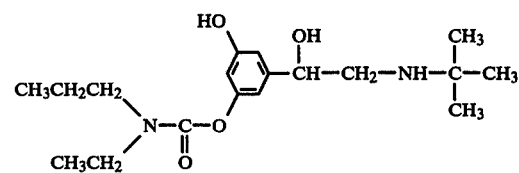
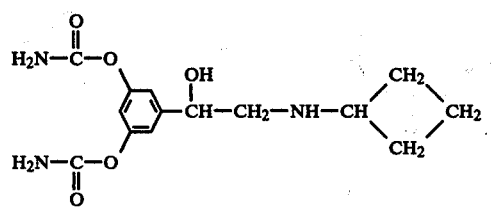
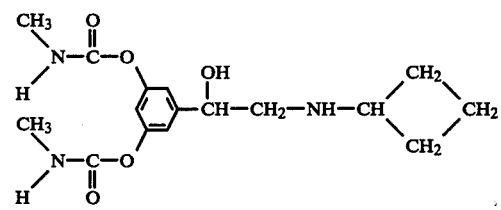
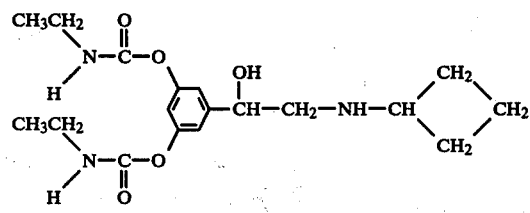
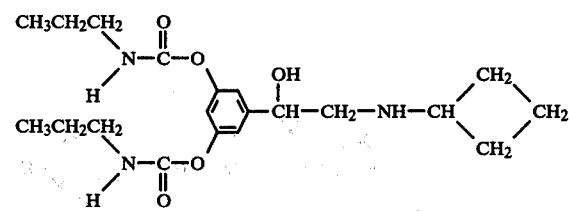
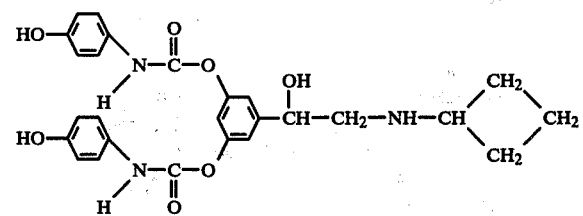
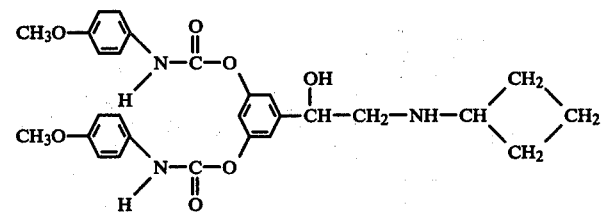

-continued
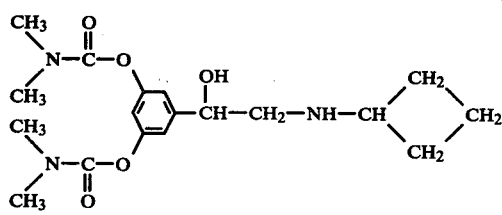
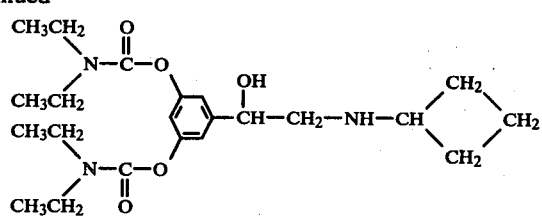
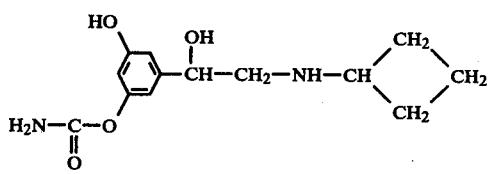
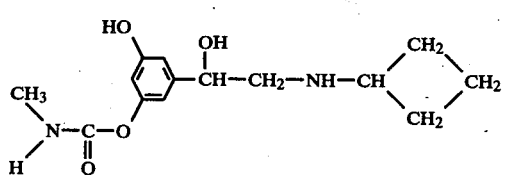
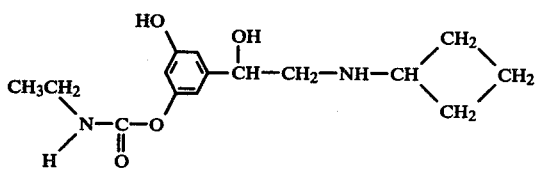
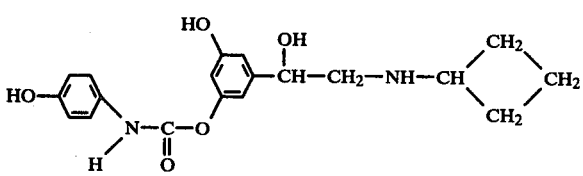
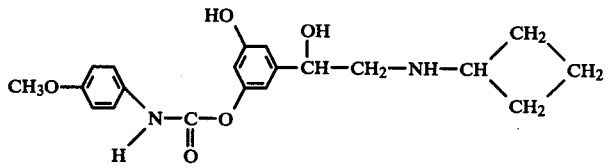
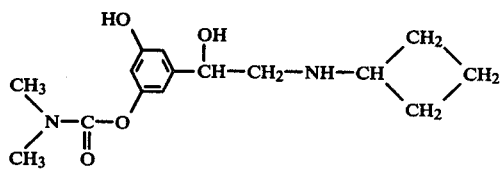
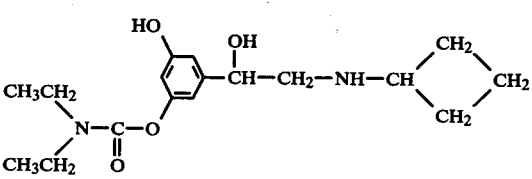
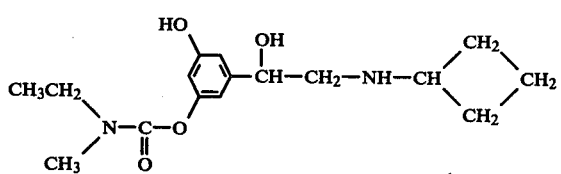
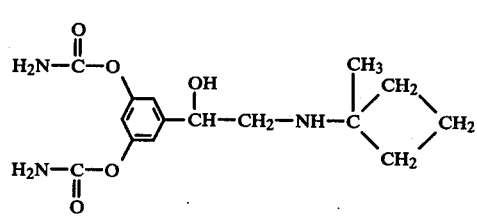
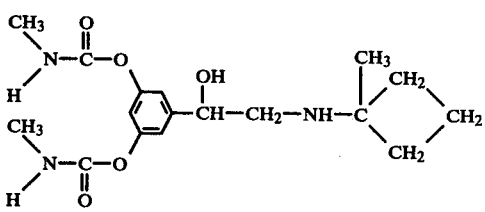
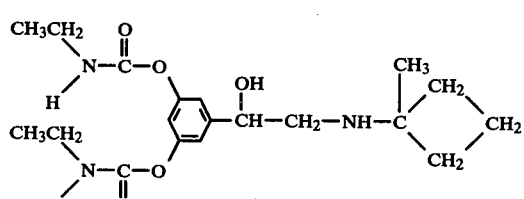

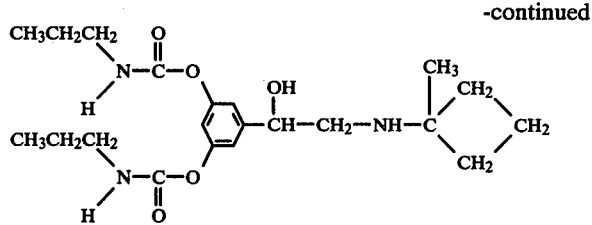
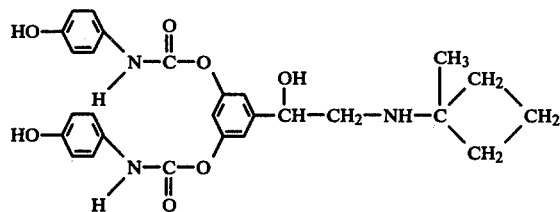
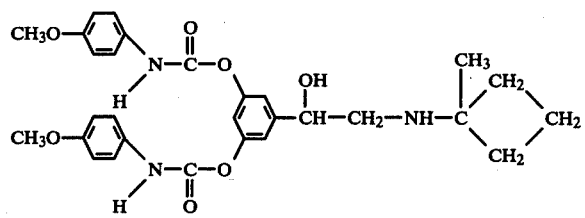
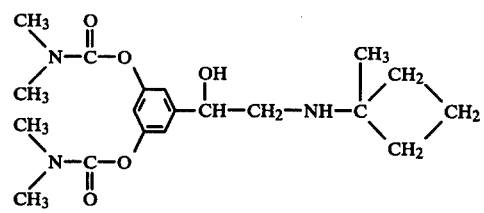
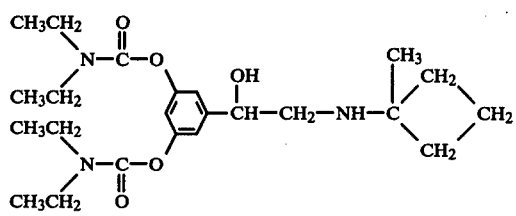
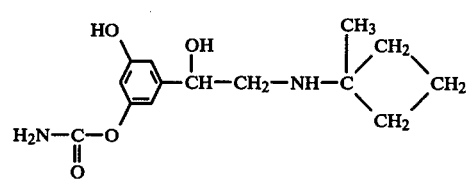
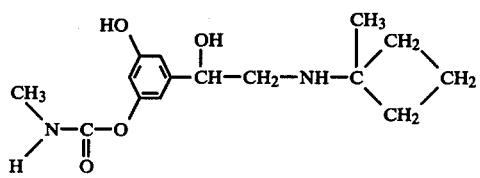
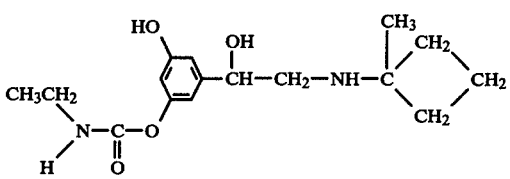
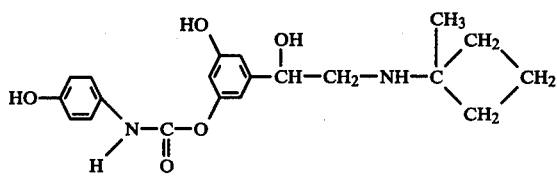
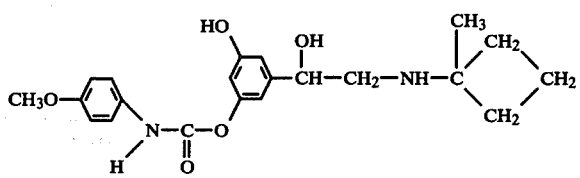
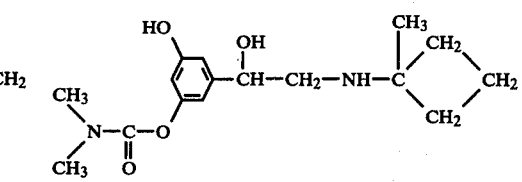
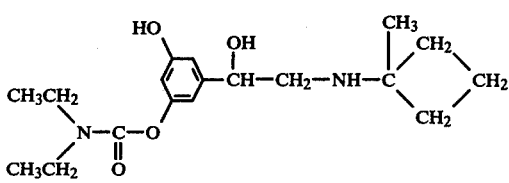
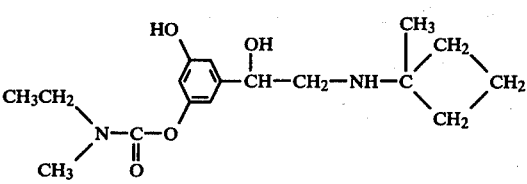
Preferred groups of compounds of the formula I are:
1. Compounds wherein R is —C(CH$_3$)$_3$ 2. Compounds of the formula

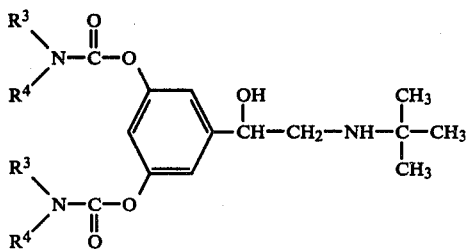

where $R^3$ and $R^4$ are H or alkyl groups having 1-3 carbon atoms.

3. Compounds of the formula

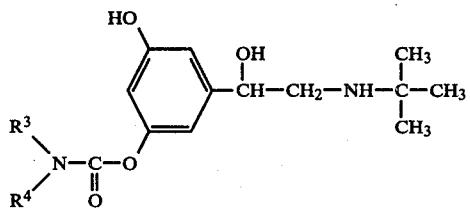

wherein $R^3$ and $R^4$ are H or alkyl groups having 1-3 carbon atoms.

4. Compounds of the formulas II and III wherein $R^3$ and $R^4$ are $CH_3$ or $CH_3CH_2$.

The preferred compound of the invention is the compound of the formula

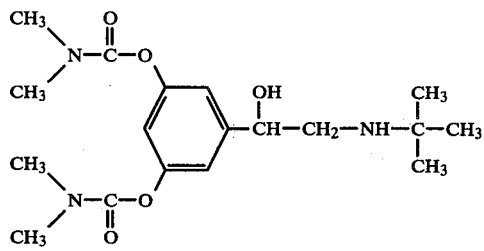

As the compounds of the invention of the formula I possess at least one asymmetric carbon atom, the invention includes all the possible optically active forms and racemic mixtures of the compounds. The racemic mixture may be resolved by conventional methods, for example by salt formation with an optically active acid, followed by fractional crystallization.

The invention also includes solvates of the compounds of the formula I such as solvates with water—½, 1 or 2 moles of water per mole compound I—and with aliphatic alcohols, 1 mole of the alcohol per mole compound I.

In clinical practice the compounds will normally be administered orally, by injection or by inhalation in the form of a pharmaceutical preparation comprising the active ingredient in the form of the original compound or optionally in the form of pharmaceutically acceptable salt thereof, in association with a pharmaceutically acceptable carrier which may be a solid, semisolid or liquid diluent or an ingestible capsule, and such preparations comprise a further aspect of the invention. The compounds may also be used without carrier material. As examples of pharmaceutical preparations may be mentioned tablets, drops, aerosol for inhalation, etc. Usually the active substance will comprise between 0.05 and 99, or between 0.1 and 99% by weight of the preparation, for example between 0.5 and 20% for preparations intended for injection and between 0.1 and 50% for preparations intended for oral administration.

The new compounds according to the invention may be administered in the form of salts with physiologically acceptable acids. Suitable acids which may be used are, for example hydrochloric, hydrobromic, sulphuric, fumaric, citric, tartaric, maleic or succinic acid.

The invention further provides pharmaceutical compositions comprising as active ingredient at least one of the compounds according to the invention in association with a pharmaceutical carrier. Such compositions may be designed for oral, bronchial, rectal or parenteral administration.

To produce pharmaceutical preparations in the form of dosage units for oral application containing a compound of the invention in the form of the free base, or a pharmaceutically acceptable salt thereof, the active ingredient may be mixed with a solid, pulverized carrier, for example, lactose, saccharose, sorbitol, mannitol, a starch such as potato starch, corn starch, maize starch or amylopection, a cellulose derivative or gelatin, and also may include lubricants such as magnesium or calcium stearate or a Carbowax or other polyethylene glycol waxes and compressed to form tablets or centers for dragees. If dragees are required, the centers may be coated, for example, with concentrated sugar solutions which may contain gum arabic, talc and/or titanium dioxide, or alternatively with a lacquer dissolved in easily volatile organic solvents or mixtures of organic solvents. Dyestuffs can be added to these coatings. For the preparation of soft gelatin capsules (pearl-shaped closed capsules) consisting of gelatin and, for example, glycerol, or similar closed capsules, the active substance may be admixed with a Carbowax. Hard gelatin capsules may contain granulates of the active substance with solid, pulverized carriers such as lactose, saccharose, sorbitol, mannitol, starches (for example potato starch, corn starch, or amylopectin), cellulose derivatives or gelatin, and may also include magnesium stearate or stearic acid. Dosage units for rectal application may be in the form of suppositories comprising the active substance in admixture with a Carbowax or other polyethylene glycol waxes. Each dosage unit preferably contains 1 to 50 mg active ingredient.

Liquid preparations for oral application may be in the form of syrups, suspensions or emulsions, for example containing from about 0.1% to 20% by weight of active substance and also, if desired, such adjuvants as stabilizing agents, suspending agents, dispersing agents, flavouring agents and/or sweetening agents.

Liquid preparations for rectal administration may be in the form of aqueous solutions containing from about 0.1% to 2% by weight of active substance and also, if desired, stabilizing agents and/or buffer substances.

For parenteral application by injection the carrier may be a sterile, parenterally acceptable liquid, e.g. pyrogen-free water or an aqueous solution of polyvinylpyrrolidone, or a parenterally acceptable oil, e.g., arachis oil and optionally stabilizing agents and/or buffer substances. Dosage units of the solution may advantageously be enclosed in ampoules, each dosage unit preferably containing from 0.1 to 10 mg of active ingredient.

For administration to the bronchia, the compositions are advantageously in the form of a spray solution or spray suspension. The solution or suspension advantageously contains from 0.1 to 10% by weight of the active ingredient.

The dosage at which the active ingredients are administered may vary within a wide range and will depend on various factors such as, for example, the individual requirements of each patient. A suitable oral dosage range may be from 5 to 200 mg per day.

At treatment with dose aerosol, a suitable dosage unit may contain from 0.1 to 10 mg of the active ingredient. One or two such dosage units may be administered at each treatment.

The pharmaceutical compositions containing the active ingredients may suitably be formulated so that they provide doses within these ranges either as single dosage units or as multiple dosage units.

It is indicated in the test results in Table 1 below that compounds of the present invention may have an onset of bronchodilating effect which is slower than the onset of the bronchodilating effect of the reference substance terbutaline. This profile of activity will make the compounds of the invention suitable for use not only by themselves in continuous maintenance therapy, but also in acute therapy in combination with bronchodilating drugs which have a faster onset of effect. As examples of known bronchospasmolytically active compounds which are suitable for use in combination with the compounds of the present invention may be mentioned terbutaline, ibuterol, orciprenaline, salbutamol, epinephrine, isoprenaline, and ephedrine.

These compounds have the following structural formulas:

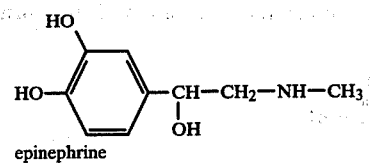
epinephrine

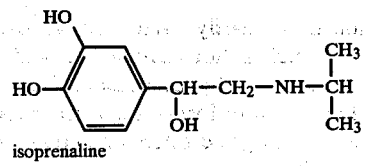
isoprenaline

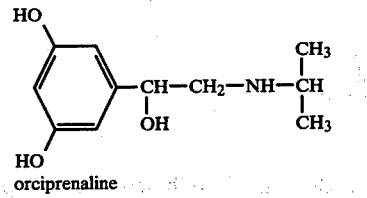
orciprenaline

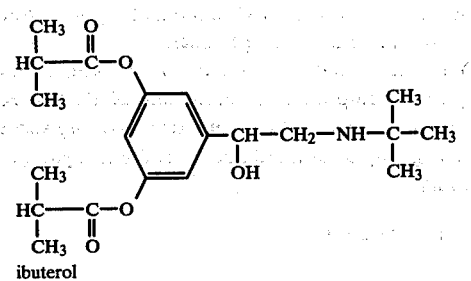
ibuterol

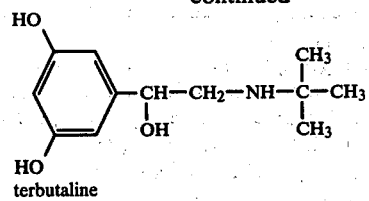
terbutaline

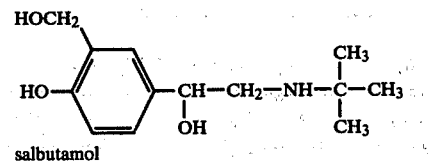
salbutamol

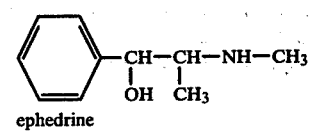
ephedrine

The following bronchospasmolytically active compounds may also be used in combination with the compounds of the invention:

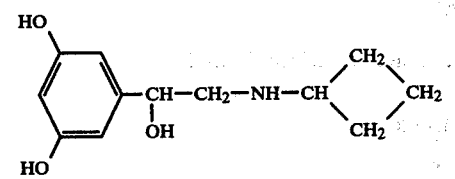

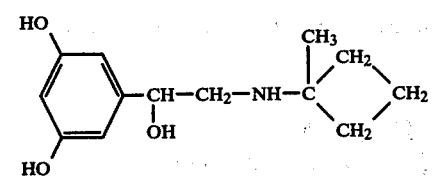

Pharmaceutical combination preparations containing a compound of the invention together with a further bronchospasmolytically active substance with faster onset of effect constitute a further aspect of the present invention.

In pharmaceutical compositions containing a combination of a compound of the formula I with a conventionally used bronchospasmolytic agent such as mentioned above, the weight proportion of the known compound to the compound I of the invention is suitably from 1:2 to 1:5 and, preferably from 1:3 to 1:4.

The compounds of the invention can be prepared by known methods such as (A) Reducing a compound of the formula

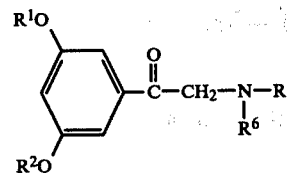

wherein R, $R^1$ and $R^2$ are as defined above, and wherein when $R^1$ or $R^2$ is H the resulting hydroxy substituents may be protected by a hydroxy-protecting group, and wherein R⁶ is hydrogen or a N-protecting group. Thereafter, if necessary, remaining protecting groups are replaced by hydrogen.

As examples of groups which can be used for protection of hydroxy substituents in the radicals R¹ and R² can be mentioned ordinarily used hydroxy-protecting groups readily replaceable by hydrogen such as, for example, alkyl or acyl radicals of not more than 5 carbon atoms or mono- or bicyclic aralkyl groups of not more than 11 carbon atoms such as benzyl or naphthylmethyl.

As examples of groups which can be used for protection of the amino nitrogen atom can be mentioned ordinarily used protecting groups such as mono- or bicyclic aralkyl groups containing not more than 11 carbon atoms such as benzyl and naphthylmethyl.

The reduction can be carried out by known methods using for example Pd/C or NaBH₄.

(B) Reacting a compound of the formula

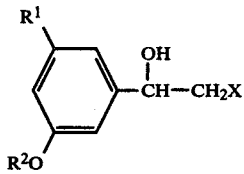

with a compound of the formula

to the formation of a compound of the formula

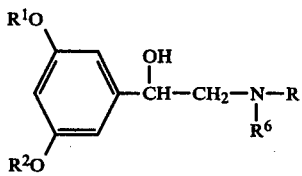

Thereafter, if necessary, protecting groups are replaced by hydrogen, in which formulas R, R¹, R² and R⁶ are as defined in method A above and wherein X is halogen or a functionally equivalent group capable of reacting with the amine HNR⁶R.

As examples of the radical X can be mentioned leaving groups such as F, Cl, Br, I, or OSO₂R⁸, wherein R⁸ is alkyl, aralkyl or aryl.

(C) Reacting a compound of the formula

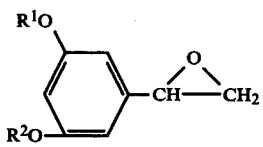

with a compound of the formula

to the formation of a compound of the formula

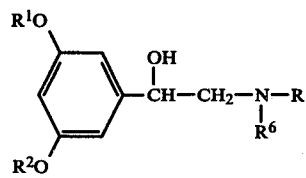

Thereafter, if necessary, protecting groups are replaced by hydrogen, in which formulas R, R¹, R² and R⁵ are as defined in method A above.

(D) Reacting a compound of the formula

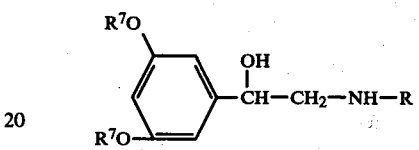

wherein R⁷ is H or a hydroxy-protecting group such as illustrated in method A, provided that at least one radical R⁷ is H, with a compound of the formula

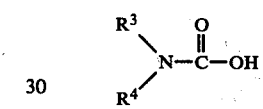

or a reactive derivative thereof, in which formula R³ and R⁴ are as defined above. Thereafter, if necessary, protecting groups are replaced by hydrogen.

As examples of reactive derivatives of the formula

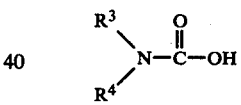

can be mentioned ordinarily used reactive carboxyl groups —CO—Y such as for example an acid halide such as acid chloride, an alkyl ester, an acid anhydride or a mixed anhydride with formic esters or carboxylic acids, sulphonic or inorganic esters or derivatives obtained by reaction between a compound

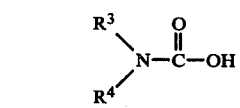

and a carbodiimide or similarly functioning compounds such as N,N'-carbonyldiimidazole or N-ethyl-5-phenylisoxazolium-3'-sulphonate.

A further reactive derivative which can be used for preparing compounds wherein one of R³ and R⁴ is H and the other is an alkyl group or a possibly substituted phenyl group as defined above, is the isocyanate of the formula

(E) Reducing a compound of the formula

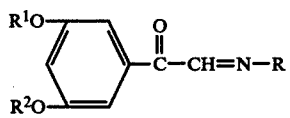

Thereafter, if necessary, protecting groups are replaced by hydrogen, in which formula, R, R¹ and R² are as defined previously.

The reduction can be carried out in known manner for example using NaBH₄.

For the preparation of such compounds of the formula I wherein R¹ is H, it will be understood that in the methods A—E illustrated above the starting material will be a 3,5-disubstituted compound such as depicted in the methods A-E where the radical —OR¹, or corresponding substituent, is a hydroxy protected group —OR⁷ where the group R⁷ is an ordinarily used hydroxy protecting group such as exemplified in method A which is replaced by hydrogen in the step where, if necessary, remaining protecting groups are replaced by hydrogen.

Benzyl is a preferred hydroxy-protecting group. Benzyl is also a preferred protecting group for the amino nitrogen.

The compounds of the formula I thus obtained are, if desired, resolved into their optical isomers. The compounds I are also, if desired, converted to pharmaceutically acceptable salts.

The intermediates used in the method A-E above are in some cases new compounds. It will be illustrated below how the intermediates can be prepared. All reactions illustrated are known. For simplification, the various routes which are possible for preparing the intermediates will be illustrated by specific examples. It will easily be understood how these specific examplifications can be applied for preparing other intermediates which may be required in the preparation of other end compounds.

In the reaction schemes below, the radical benzyl will be designated Bz.

Routes of preparation for intermediates used in Method A

Route A1:

Step 1

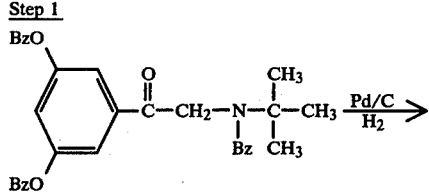

Step 2

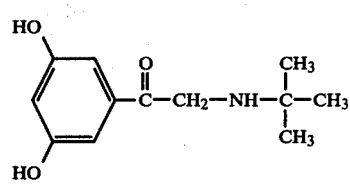

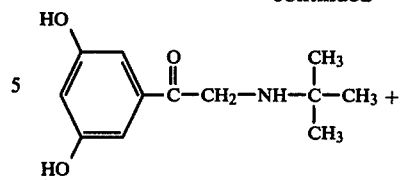

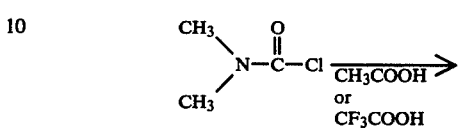

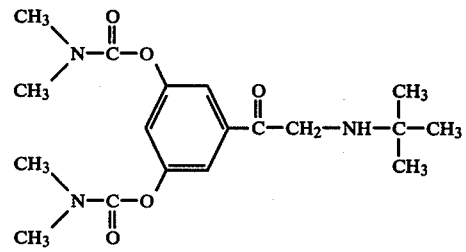

Route A2:

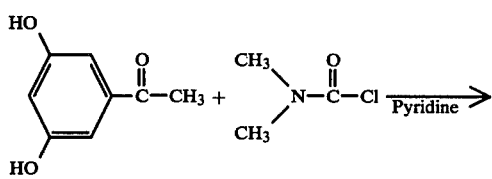

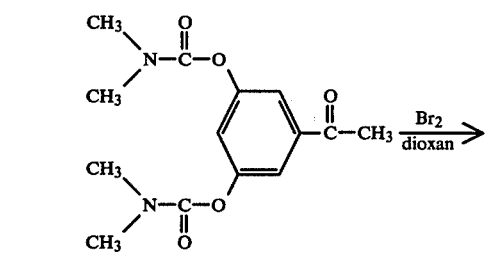

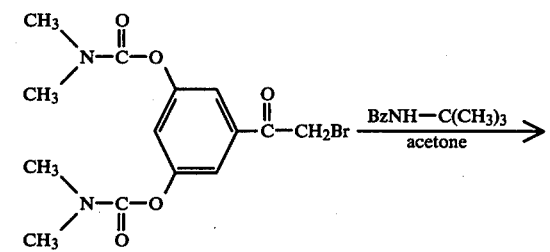

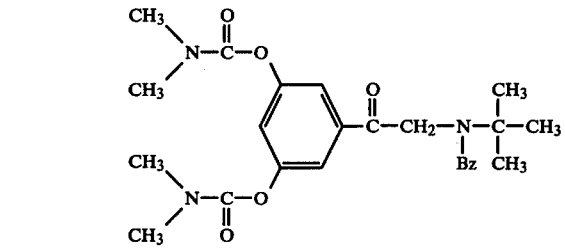

Route of preparation for intermediates used in Method B

-continued

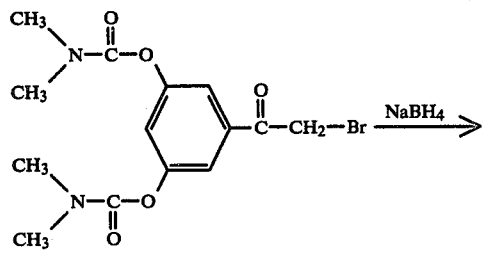

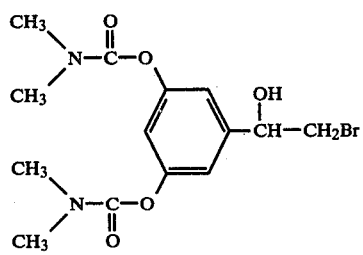

Route of preparation for intermediates used in Method C

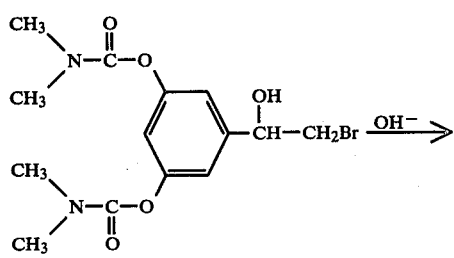

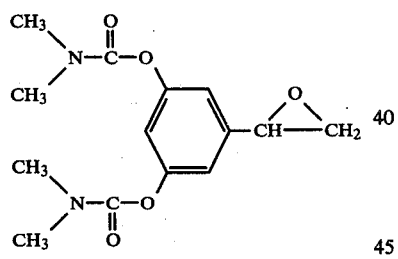

The intermediate used in Method D is the known compound terbutaline which may be prepared as described, for example, in U.S. Pat. No. 4,011,258.

Route of preparation for intermediates used in Method E

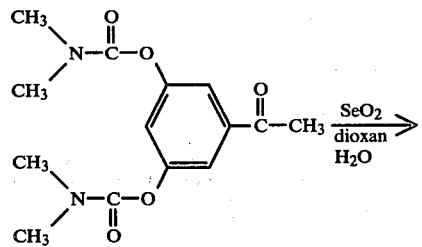

-continued
Route of preparation for intermediates used in Method E

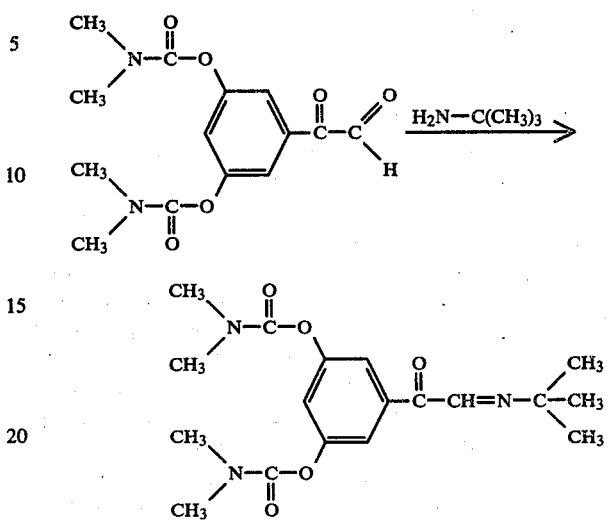

The starting material of the formula

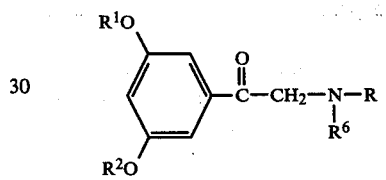

where R, $R^1$, $R^2$ and $R^6$ are as defined in Method A, are novel and constitute as such a further aspect of the invention.

Also the starting material used in Method E:

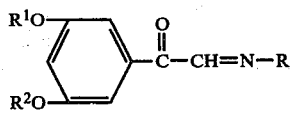

wherein R, $R^1$ and $R^2$ are as defined in Method A, are novel and constitute an aspect of the invention.

Such intermediates in Methods B, C and D which are end products of the formula I having hydroxy protecting groups or nitrogen protecting groups are also novel and constitute further aspects of the invention.

The invention is illustrated by the following examples.

EXAMPLE 1

Preparation of
1-[bis-(3',5'-N,N-dimethylcarbamoyloxy)phenyl]-2-N-tert.butylaminoethanol hydrochloride A solution of 78 g of bis-3',5'-(N,N-dimethylcarbamoyloxy)-2-(N-benzyl-t-butyl)-amino acetophenone in 300 ml of ethanol was hydrogenated in a Parr equipment in the presence of 25 ml of benzyl chloride and 3.5 g of 10% Pd/C. The hydrogenation time was 24 hrs at a pressure of 345 KPa (50 psig) and a temperature of 50° C. The catalyst was filtered off, and the filtrate was evaporated to dryness. The residue was dissolved in isopropanol, filtered, and to the filtrate was added diethylether to precipitate the title compound. The identity of the title product obtained was confirmed with NMR.

Yield: 46.5 g.

NMR δ ppm: 1.3 9H (s); 3.0 12H (d); 3.2 2H (m); 4.6 DOH); 5.0 1H (q); 7.0 3H (m) (D₂O).

GCMS: 99.8%.

Cl⁻$_{calc}$: 8.8% Cl⁻$_{found}$: 8.8%.

HPLC: 100.0%.

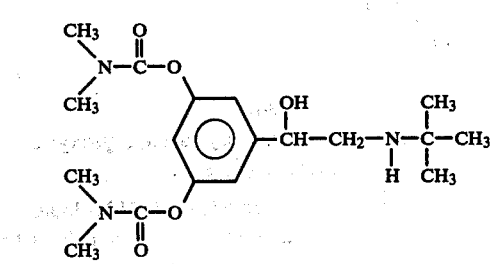

The bis-3',5'-(N,N-dimethylcarbamoyloxy)-2-(N-benzyl-t-butyl)amino acetophenone which was used as starting material was prepared as follows.

(1a)
Bis-3,5-(N-N-dimethylcarbamoyloxy)-acetophenone

To a solution of 152 g 3,5-dihydroxyacetophenone in 700 ml dry pyridine was added 280 ml of N,N-dimethylcarbamoyl chloride. The mixture was stirred for 18 hrs at 60°-70° C. After evaporation in vacuo the residue was treated with a mixture of diethylether and water. The water phase was extracted with diethylether. Thereafter the combined diethylether phases were washed with water, and dried over MgSO₄. After evaporation, the residue was recrystallized from isopropylalcohol-petroleum ether b.p. 40°-60° C. The identity of the product was confirmed with NMR.

Yield: 180.4 g.

NMR δ ppm: 2.6 3H (s); 3.1 12H (s); 7.4 3H (m) (CDCl₃, TMS).

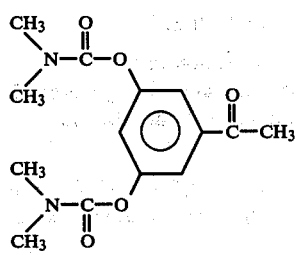

(1b)
Bis-3',5'-(N,N-dimethylcarbamoyloxy)-2-bromoacetophenone

To a solution of 180 g of bis-3,5-(N,N-dimethylcarbamoyloxy)-acetophenone obtained in step 1a in 700 ml of dioxane was added dropwise a solution of 31 ml of bromine in 200 ml of dioxane. The mixture was stirred at 35° C. for 1 hr. The residue obtained after evaporation in vacuo was recrystallized from isopropylalcohol-petroleum ether b.p. 40°-60° C. The identity of the product was confirmed with NMR.

Yield: 174 g.

NMR δ ppm: 3.1 12H (s); 4.5 2H (s); 7.4 3H (m) (CDCl₃, TMS).

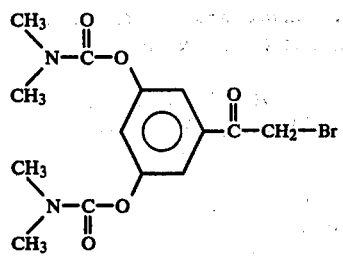

(1c)
Bis-3',5'-(N,N-dimethylcarbamoyloxy)-2-(N-benzyl-t-butyl)amino acetophenone To a solution of 5.6 g of the bromo-acetophenone obtained in step 1b in 75 ml of acetone was added a solution of 4.9 g of N-benzyl-t-butylamine in 30 ml of acetone. The mixture was refluxed under stirring for 18 hrs, filtered, and evaporated in vacuo. The residue was dissolved in diethyl ether, petroleum ether b.p. 61°-70° C. was added, and the yellow precipitate formed filtered off. After washing with water followed by a 1:1 mixture of isopropylalcohol-petroleum ether while crystals were obtained.

The identity of the product was confirmed with NMR.

Yield: 4.6 g.

NMR δ ppm: 1.2 9H (s); 3.1 12H (s); 3.9 2H (s); 4.0 2H (s); 7.3 8H (m) (CDCl₃, TMS).

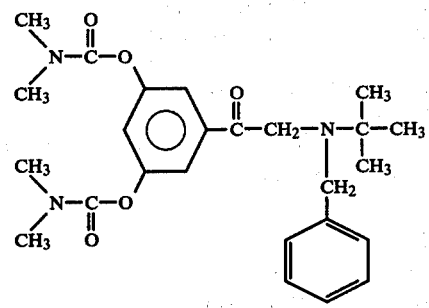

EXAMPLE 2

Preparation of 1-[3-(N,N-dimethylcarbamoyloxy)-5-hydroxy]-phenyl-2-t-butylamino-ethanol hydrochloride (a)
3'-Benzyloxy-5'-(N,N-dimethylcarbamoyloxy)-2-N-benzyl-t-butylamino-acetophenone hydrochloride To a solution of 9.1 g of 3-benzyloxy-5-(N,N-dimethylcarbamoyloxy)-acetophenone in 150 ml of acetone was added 7.5 g of N-benzyl-t-butylamine in 50 ml of acetone. The mixture was stirred under reflux for 4 days. Thereafter it was evaporated. The residue was dissolved in diethylether, and the precipitated (5.5 g) N-benzyl-t-butylamine hydrobromide was filtered off. To the filtrate was added 2 N HCl, and the ether phase was discarded. The aqueous phase was neutralized with 10% sodium carbonate solution and extracted with diethylether. The ether phase was dried over MgSO₄ and filtered. Thereafter it was acidified with etheral hydrogen chloride. The precipitated brown oil was separated and dissolved in ethanol (25 ml). The title compound crystallized upon the addition of diethylether to the ethanol solution. The identity of the product was confirmed with NMR.

Yield: 5.3 g.

NMR δ ppm: 2.05 9H (s); 3.25 6H (d); 5.15 2H (s); 5.45 2H (s); 7.75 13H (m) (CDCl₃, TMS).

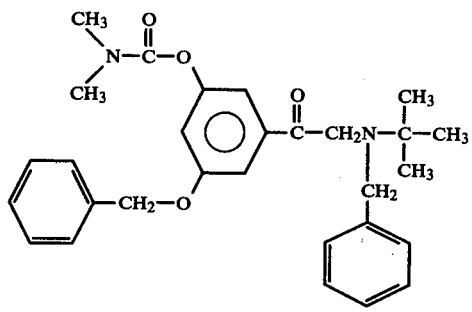

(b)
1-[3-(N,N-dimethylcarbamoyloxy)-5-hydroxy]-phenyl-2-t-butylamino-ethanol hydrochloride A solution of 3'-Benzyloxy-5'-N,N-dimethylcarbamoyloxy-2-N-benzyl-t-butylamino-acetophenone hydrochloride obtained in step a in 75 ml of ethanol was hydrogenated in the presence of 1 g 10% Pd/C at ambient temperature and 380 KPa (55 psig) for 18 hours. The catalyst was filtered off and the filtrate evaporated to dryness. The residue was recrystallized from isopropylalcohol/diethylether. The identity of the title compound was confirmed with NMR.

Yield: 1.6 g.
GCMS: (di-TMS-derivative) 99%.
HPLC: 99%.
NMR δ ppm: 1.40 9H (s); 3.05 6H (d); 3.12 2H (m); DOH 4.70; 4.95 1H (q); 6.70 3H (m) (D₂O).

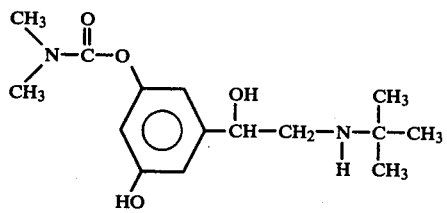

The 3-benzyloxy-5-(N,N-dimethylcarbamoyloxy)-acetophenone which was used as starting material was prepared as follows.

(2a)
3-Benzyloxy-5-(N,N-dimethylcarbamoyloxy)-acetophenone

To a solution of 9.7 g of 3-benzyloxy-5-hydroxyacetophenone in 200 ml of pyridine was added 5.5 ml of dimethyl carbamoyl chloride. After stirring the mixture at 50°–70° C. for 18 hours, it was evaporated to dryness, and the residue partitioned between diethylether H₂O. Evaporation of the ether phase gave a yellow oil which was purified by column chromatography on Silica gel 60 with CHCl₃/p-ether b.p. 40°–60° C. (8:2) as eluant.

Yield: 11.3 g.
NMR δ ppm: 2.55 3H (s); 3.10 6H (s); 5.10 2H (s); 7.30 8H (m) (CDCl₃, TMS).

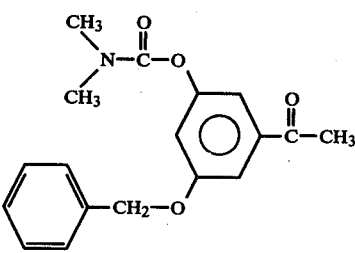

(2b)
3'-Benzyloxy-5'-(N.N-dimethylcarbamoyloxy)-2-bromoacetophenone

To a solution of 11.3 g 3-benzyloxy-5-(N.N-dimethylcarbamoyloxy)-acetophenone obtained in step 2a in 150 ml of dioxane was added dropwise 1.8 ml of bromine in 50 ml of dioxane. The mixture was stirred at ambient temperature for 1 hour, and then evaporated. The residue was dissolved in diethylether and treated with activated charcoal. After filtering, the filtrate was evaporated, and the residue recrystallized from isopropanol. The identity of the product was confirmed with NMR.

Yield: 7.9 g.
NMR δ ppm: 3.10 6H (s); 4.40 2H (s); 5.10 2H (s); 7.28 8H (m) (CDCl₃, TMS).

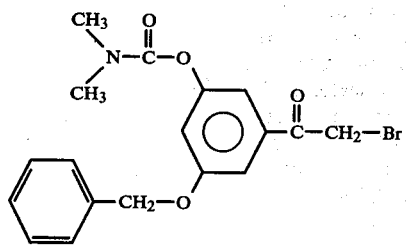

EXAMPLE 3

Preparation of 1-[3',5'-bis-(N-ethylcarbamoyloxy]-phenyl-2-t-butylaminoethanol hydrochloride (a)
3',5'-Bis-(N-ethylcarbamoyloxy)2-N-benzyl-t-butylamino acetophenone hydrochloride To a solution of 8.0 g of 3',5'-bis-(N-ethylcarbamoyloxy)-2-bromo acetophenone in 100 ml of acetone was added 7.0 g of N-benzyl-t-butylamine. The mixture was refluxed for 18 hours. The 4.1 g of N-benzyl-t-butylamine hydrobromide formed and precipitated during the reaction was filtered off and the filtrate was acidified with conc. HCl. The filtrate was now evaporated to dryness and the title compound was isolated by column chromatography on Silica gel 60 using (1) CHCl₃/ethanol (2:1), (2) ethanol as eluants. The title compound was eluted in the ethanol fraction and recrystallized from ethanol/diethylether. The identity of the product was confirmed with NMR.

Yield: 0.3 g.
NMR δ ppm: 1.2 6H (t); 1.6 9H (s); 3.3 6H (m); 4.2 2H (m) 4.9 2H (s); 7.4 8H(m) (CD₃OD, TMS).

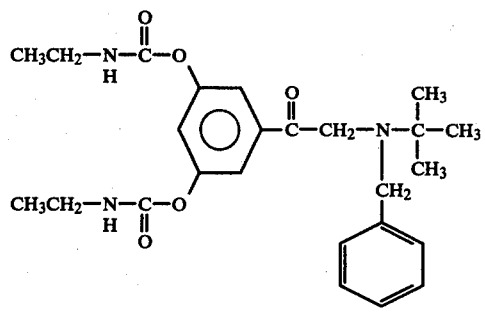

(b)

1-[3′,5′-Bis-(N-ethylcarbamoyloxy]-phenyl-2-t-butylaminoethanol hydrochloride

A solution of the aminoacetophenone—0.3 g—in 50 ml of methanol was hydrogenated in the presence of 0.1 g Pd/C at ambient temperature and 345 kpa (50 psig) for 18 hours. The catalyst was filtered off and the filtrate was evaporated to dryness. The residue was dissolved in isopropanol and diethylether was added to precipitate the title compound. The identity of the title product obtained was confirmed with NMR.

Yield: 0.18 g.
GCMS: TMS derivative.
NMR δ ppm: 1.2 6H (t); 1.5 9H (s); 3.3 6H (m); 5.3 1H (m) 6.1 2H (t); 6.9 3H (m) (CDCl₃, TMS).
HPLC: 98.4%.

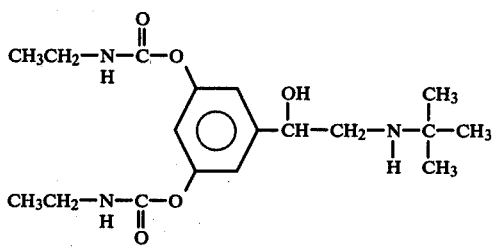

The 3′,5′-bis-(N-ethylcarbamoyloxy-2-bromo)acetophenone which was used as starting material was prepared as follows.

(3a) 3,5-Bis-(N-ethylcarbamoyloxy)-acetophenone

To a solution of 15 g of 3,5-dihydroxy acetophenone in 200 ml of pyridine was added 18.8 ml of ethyl isocyanate. The mixture was stirred at 70° C. for 18 hours. Thereafter it was evaporated. The residue was partitioned between chloroform/water; the chloroform phase was washed with diluted hydrochloric acid, and then evaporated. The crystalline residue was recrystallized from isopropanol. The identity of the product was confirmed with NMR.

Yield: 19.4 g.
NMR δ ppm: 1.2 6H (t); 2.6 3H (s); 3.35 4H (p); 5.45 2H (t); 7.3 1H (q); 7.6 2H (d) (CDCl₃, TMS).

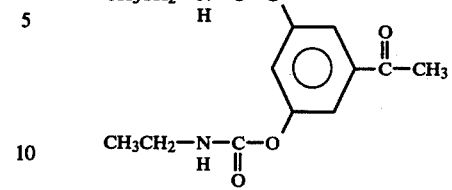

(3b)

3′,5′-Bis-(N-ethylcarbamoyloxy)-2-bromo-acetophenone

To a solution of 19.4 g of the acetophenone obtained in step 3a in 300 ml of dioxane was added 3.7 ml of bromine in 100 ml of dioxane. The mixture was stirred at ambient temperature for 1 hour. Thereafter it was evaporated and the residue crystallized from isopropanol. The identity of the product was confirmed with NMR.

Yeld: 16.7 g.
NMR δ ppm: 1.2 6H (t); 3.3 4H (p); 4.45 2H (s); 5.35 2H (t); 7.3 1H (q); 7.6 2H (d); (CDCl₃, TMS).

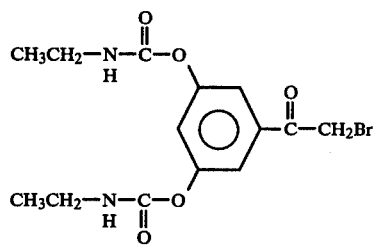

EXAMPLE 4

Preparation of 1-[Bis-(3′,5′-(N,N-dimethylcarbamoyloxy)phenyl]-2-cyclobutylaminoethanol sulphate A solution of 2.9 g of bis-3′,5′-(N,N-dimethylcarbamoyloxy)-2-(N-benzyl-cyclobutyl)-amino acetophenone hydrochloride in 50 ml of ethanol was hydrogenated at a pressure of 345 KPa (50 psig) and 45° C. for 18 hrs in the presence of 0.5 g 10% Pd/C.

The oil obtained after filtering off the catalyst and evaporation of the filtrate was dissolved in water which was made alkaline with 1 M sodium carbonate solution and then extracted with diethyl ether. The residue after evaporation was dissolved in ethanol and ethanolic sulphuric acid was added to pH 5.5. After evaporation a crystalline residue was obtained which was recrystallized from isopropanol. The identity of the product was confirmed with NMR.

Yield: 1 g.
CIMS (NH₃): the calculated molecular weight was observed. $SO_4^{2-}$: 98.7%.
NMR (D₂O) δ ppm: 2.05 6H (m); 3.00 14H (m); 3.65 1H (m); 4.60 (DOH); 4.95 1H (m); 6.95 3H (m).

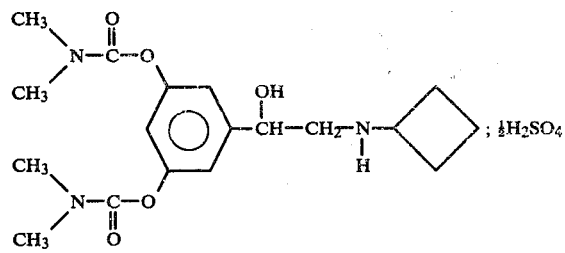

The bis-3',5'-(N,N-dimethylcarbamoyloxy)-2-(N-benzylcyclobutyl)-amino acetophenone hydrochloride which was used as starting material was prepared as follows:

4a.
Bis-3',5'-(N,N-dimethylcarbamoyloxy)-2-(N-benzylcyclobutyl)-amino acetophenone hydrochloride A solution of 4.9 g (0.013 moles) of bis-3',5'-(N,N-dimethylcarbamoyloxy)-2-bromo-acetophenone and 4.4 g (0.027 moles) of N-benzyl-cyclobutylamine in 120 ml dry acetone was refluxed with stirring for 18 hrs. After filtering and evaporation to dryness the residue was dissolved in dry ethyl ether. Ethanolic hydrogen chloride was then added to the ether solution until pH 2. After evaporation of the ether solution a brown oil was obtained which crystallized from acetone/ethylether.

Yield: 5.5 g which was dissolved in chloroform and purified by chromatography on Silica gel 60 using $CHCl_3/C_2H_5OH$ 10:1 as an eluant. The fraction containing the title compound was then evaporated to yield 2.9 g crystalline material. The identity of the product was confirmed with NMR.

NMR ($CDCl_3$) δ ppm: 2.0 4H (m); 2.8 2H (m); 3.05 12H (d); 4.4 5H (m); 7.5 8H (m).

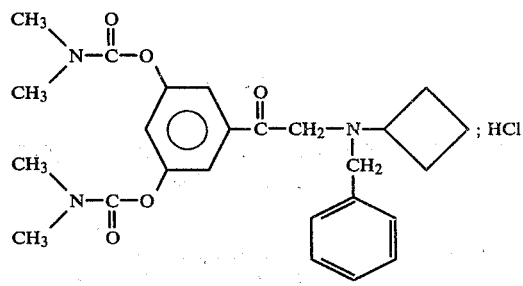

EXAMPLE 5

Preparation of 1-[Bis-(3',5'-(N,N-dimethylcarbamoyloxy)phenyl]-2-(1-methyl)-cyclobutylaminoethanol hydrochloride A solution of 6 g of bis-3',5'-(N,N-dimethylcarbamoyloxy-2-N-benzyl-(1-methyl)-cyclobutylamino acetophenone hydrochloride in 100 ml of ethanol was hydrogenated at a pressure of 380 KPa (55 psig) and 45° C. for 18 hrs in the presence of 0.5 g 10% Pd/C. After filtering off the catalyst, the filtrate was evaporated to dryness, and the residue crystallized from isopropanol/diethylether. The identity of the compound was confirmed with NMR.

Yield: 4.3 g.

HPLC: 98.9% purity.

$Cl^-_{calc}$: 8.5% $Cl^-_{found}$: 8.4%.

NMR: ($D_2O$) δ ppm: 1.50 3H (s); 2.10 6H (m); 3.08 14H (m); 4.70 (DOH); 5.08 1H (m); 7.08 3H (m).

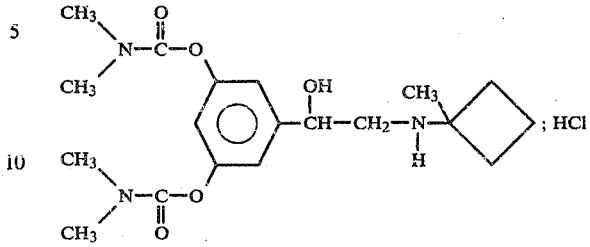

The bis-3',5'-(N,N-dimethylcarbamoyloxy-2-N-benzyl-(1-methyl)cyclobutylamino acetophenone hydrochloride which was utilized as starting material was prepared as follows:

5a.
Bis-3',5'-(N,N-dimethylcarbamoyloxy)-2N-benzyl-(1-methyl)-cyclobutylamino acetophenone hydrochloride A solution of 6.7 g (0.018 moles) of bis-3',5'-(N,N-dimethylcarbamoyloxy)-2-bromoacetophenone and 6.9 g (0.039 moles) of N-benzyl-1-methylcyclobutylamine in 100 ml of dry acetone was boiled under reflux for 18 hours. The reaction mixture was filtered, and the filtrate evaporated to dryness. The residue was dissolved in diethyl ether to which ethanolic hydrogen chloride was added to pH 2. After evaporation the residue was recrystallized from ethanol/diethyl ether. The identity of the product was confirmed with NMR.

Yield: 6 g.

NMR ($CDCl_3$) δ ppm: 1.75 3H (s); 2.0 4H (m); 3.15 14H (m); 4.67 4H (m); 7.58 8H (m).

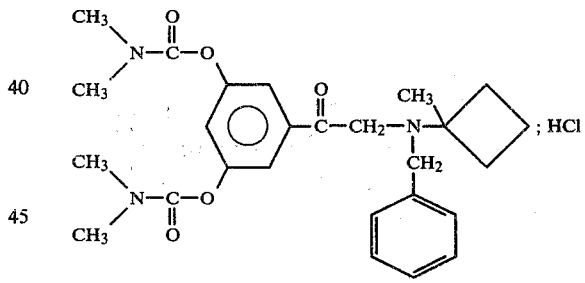

The following examples illustrate how the compounds of the invention can be incorporated in pharmaceutical compositions:

EXAMPLE 6

Aerosol for inhalation

1-[bis(3',5'-(N,N-dimethylcarbamoyloxy)phenyl]-2-N-tert.butylaminoethanol hydrochloride: 0.75 g
Niglyol ®: 0.20 g
Frigen ® 11/12/113/114: ad 100.0 g

EXAMPLE 7

Tablets

Each tablet contains:

| | |
|---|---|
| 1-[bis(3',5'-(N,N—dimethylcarbamoyloxy)phenyl]-2-N—tert.butylaminoethanol hydrochloride | 6.0 mg |
| Maize starch | 25.0 mg |
| Lactose | 206.0 mg |

-continued

| | |
|---|---|
| Gelatin | 1.5 mg |
| Talc | 10.0 mg |
| Magnesium stearate | 1.5 mg |
| | 250.0 mg |

EXAMPLE 8

Suppositories

Each suppository contains:
1-[bis(3',5'-(N,N-dimethylcarbamoyloxy)phenyl]-2-N-tert.butylaminoethanol hydrochloride: 6.0 mg
Ascorbyl palmitate: 1.0 mg
Suppository base (Imhausen H): ad 2.000.0 mg

EXAMPLE 9

Syrup

1-[bis(3',5'-(N,N-dimethylcarbamoyloxy)phenyl]-2-N-tert.butylaminoethanol hydrochloride: 0.060 g
Liquid glucose: 30.0 g
Sucrose: 50.0 g
Ascorbic acid: 0.1 g
Sodium pyrosulfite: 0.01 g
Disodium edetate: 0.01 g
Orange essence: 0.025 g
Certified colour: 0.015 g
Purified water: ad 100.0 g

EXAMPLE 10

Inhalation solution

1-[bis(3',5'-(N,N-dimethylcarbamoyloxy)phenyl]-2-N-tert.butylaminoethanol hydrochloride: 0.75 g
Sodium pyrosulfite: 0.10 g
Disodium edetate: 0.10 g
Sodium chloride: 0.85 g
Purified water: ad 100.0 ml

EXAMPLE 11

Solution for rectal administration (Rectal vials)

1-[bis(3',5'-(N,N-dimethylcarbamoyloxy)phenyl]-2-N-tert.butylaminoethanol hydrochloride: 6.0 mg
Sodium pyrosulfite: 1.5 mg
Disodium edetate: 0.3 mg
Sterile water: ad 3.0 ml

EXAMPLE 12

Sublingual tablets

| | |
|---|---|
| 1-[bis(3',5'-(N,N—dimethylcarbamoyloxy)phenyl]-2-N—tert.butylaminoethanol hydrochloride | 3.0 mg |
| Lactose | 83.0 mg |
| Agar | 5.0 mg |
| Talc | 5.0 mg |
| | 100.0 mg |

EXAMPLE 13

Drops

1-[bis(3',5'-(N,N-dimethylcarbamoyloxy)phenyl]-2-N-tert.butylaminoethanse hydrochloride: 0.60 g
Ascorbic acid: 1.00 g
Sodium pyrosulfite: 0.10 g
Disodium edetate: 0.10 g
Liquid glucose: 50.00 g
Absolute alcohol: 10.00 g
Purified water: ad 100.0 ml

EXAMPLE 14

Tablets

Each tablet contains:

| | |
|---|---|
| 1-[bis(3',5'-(N,N—dimethylcarbamoyloxy)phenyl]-2-N—tert.butylaminoethanol hydrochloride | 6.0 mg |
| 1-(3',5'-dihydroxyphenyl)-2-t-butylaminoethanol sulphate (terbutaline) | 2.0 mg |
| Maize starch | 25.0 mg |
| Lactose | 204.0 mg |
| Gelatin | 1.5 mg |
| Talc | 10.0 mg |
| Magnesium stearate | 1.5 mg |
| | 250.0 mg |

EXAMPLE 15

Tablets

Each tablet contains:

| | |
|---|---|
| 1-[bis(3',5'-(N,N—dimethylcarbamoyloxy)phenyl]-2-N-tert.butylaminoethanol hydrochloride | 6.0 mg |
| α-(tert.)-butylaminomethyl-4-hydroxy-m-xylene-α-diolsulphate (salbutamol) | 2.0 mg |
| Maize starch | 25.0 mg |
| Lactose | 204.0 mg |
| Gelatin | 1.5 mg |
| Talc | 10.0 mg |
| Magnesium stearate | 1.5 mg |
| | 250.0 mg |

EXAMPLE 16

Tablets

Each tablet contains:

| | |
|---|---|
| 1-[bis(3',5'-(N,N—dimethylcarbamoyloxy)phenyl]-2-N—tert.butylaminoethanol hydrochloride | 6.0 mg |
| 1-(3',5'-diisobutyryloxy-phenyl)-2-(t-butylamino)-ethanol, hydrochloride (ibuterol) | 2.0 mg |
| Maize starch | 25.0 mg |
| Lactose | 204.0 mg |
| Gelatin | 1.5 mg |
| Talc | 10.0 mg |
| Magnesium stearate | 1.5 mg |
| | 250.0 mg |

EXAMPLE 17

Tablets

Each tablet contains:

| | |
|---|---|
| 1-[bis(3',5'-(N,N,dimethylcarbamoyloxy)phenyl]-2-N—tert.butylaminoethanol hydrochloride | 6.0 mg |
| 1-(3',5'-dihydroxyphenyl)-2-(i-propylamino)-ethanol sulphate (orsiprenaline) | 2.0 mg |
| Maize starch | 25.0 mg |
| Lactose | 202.0 mg |
| Gelatin | 1.5 mg |
| Talc | 10.0 mg |
| Magnesium stearate | 1.5 mg |
| | 250.0 mg |

EXAMPLE 18

Syrup

1-[bis(3',5'-(N,N-dimethylcarbamoyloxy)phenyl]-2-N-tert.butylaminoethanol hydrochloride: 0.60 g
1-(3',5'-dihydroxyphenyl)-2-(t-butylamino)ethanol sulphate (terbutaline): 0.020 g
Liquid glucose: 30.0 g
Sucrose: 50.0 g
Ascorbic acid: 0.1 g
Sodium pyrosulfite: 0.01 g
Disodium edetate: 0.01 g
Orange essence: 0.025 g
Certified colour: 0.015 g
Purified water: ad 100.0 ml

Pharmacological tests

A. Duration of serum levels of terbutaline after administration of compounds of the invention to unanaesthetitized dogs

Test Method

Method

Five dogs (Beagle, ♂, 13–18 kg) have been used repeatedly in the study. Each dog was used at most once a week. Food was withheld from the animals the night before the experiment (water ad libitum). The test compound was dissolved in 8 ml of distilled water, and delivered into the back of the mouth by use of a syringe and a short tube. This oral supply was followed by a water rinse of 8 ml.

The blood was collected from the cephalic veins in the forelegs by use of evacuated tubes. The esterase inhibitor diisopropylfluophosphate (DFP) was added, the samples centrifugated (+5°) and the amount of terbutaline in plasma determined by a massfragmentographic analysis method. The serum level of terbutaline indicates the degree of bronchospasmolytic effect of the test compounds.

The amounts of the test substances to be administered were selected so that the level of terbutaline corresponds to the serum levels obtained and found effective in patients at clinical use, that is a level of terbutaline of at least 2 ng/ml serum for 6 to 8 hours. The doses of the test substances of the invention were selected so that the serum levels of terbutaline obtained would correspond approximately with the serum levels obtained after administration of terbutaline per se.

Test Results

The test results are given in Table 1 below, where the time course of the serum level of terbutaline in the test animals is given. Each set of serum levels is the result of test in one dog. The boxed time interval represents the interval where a clinically effective serum level of terbutaline is obtained. Thus, the boxed interval represents the clinically useful duration of the test compounds.

TABLE 1

Serum levels ng/ml of terbutaline after p.o administration of terbulaine and various terbutaline esters to dogs Test compound:

$$R^1O-\underset{R^2O}{\underset{|}{\bigcirc}}-\underset{\underset{OH}{|}}{CH}-CH_2-NH-C(CH_3)_3$$

| Compound No. | $R^1$ | $R^2$ | Administered amount of test substance (mg/kg) | Serum level of terbutaline (ng/ml) obtained after (hours after administration) | | | | | | | | |
|---|---|---|---|---|---|---|---|---|---|---|---|---|
| | | | | 1 | 2 | 3 | 4 | 6 | 8 | 12 | 16 | 24 |
| | H | H (terbutaline, reference) | 0.1 | 5.7 | 13.7 | 9.2 | 6.1 | 3.4 | 2.2 | 1.1 | 0.8 | 0.35 |
| | H | H | 0.03 | 4.8 | 2.9 | 2.4 | 2.2 | 1.9 | (not measured) | | | |
| I | $\underset{CH_3}{\overset{CH_3}{\diagdown}}N-\overset{O}{\overset{\|}{C}}-$ | $\underset{CH_3}{\overset{CH_3}{\diagdown}}N-\overset{O}{\overset{\|}{C}}-$ | 0.6 | 0.5 | [2.2 | 4.0 | 7.3 | 8.0 | 7.1 | 5.5 | 3.8 | 1.9] |
| II | $\underset{H}{\overset{CH_3CH_2}{\diagdown}}N-\overset{O}{\overset{\|}{C}}-$ | $\underset{H}{\overset{CH_3CH_2}{\diagdown}}N-\overset{O}{\overset{\|}{C}}-$ | 1.0 | [10.3 | — | 10.0 | 9.4 | 6.7 | 5.0 | 3.1 | 2.0] | 0.9 |

It is seen in Table 1 that the test substances of the invention gives a serum level of 2 ng/ml or more for 16 hours or more. The reference substance terbutaline gives a corresponding serum level for about 8 hours, which is the duration normally obtained at clinical use of terbutaline.

B. Bronchodilating effect of the compounds of the invention per se

B1. In vitro test on isolated guinea-pig trachea

Test method

The trachea from guinea-pigs was dissected out, cut spirally and transferred to a 10 ml organ bath containing Krebs solution of 37° and aerated with carbogen. The tracheal strip was contracted by pilocarpine ($4 \cdot 10^{-6}$ mol/l) producing a tension of about 1.5 g. Isometric recording was made by use of a transducer FTO3 and Grass polygraph 7D. Before the administration of the test compound the esterase inhibitor eserin was added to the bath in a concentration of $1 \cdot 10^{-6}$ mol/l. The concentration of the test substances which produces 50% relaxation (EC50) of the pilocarpine contracted trachea was recorded as well as potentiating or inhibiting influence of the test substances of the invention on the relaxing effect of terbutaline. In this last mentioned test the muscle preparation was pretreated with the test compounds during 5 minutes, before the response of terbutaline was recorded.

Test results

The test results are given in Table 2 below.

TABLE 2

Bronchodilating effect on isolated tracheal muscle from guinea-pig

| Compound No. | Test compound R¹O—/OH/—CH—CH₂—NH—C(CH₃)₃ (R²O) R1 | R2 | Concentration of test substance producing 50% relaxation of the trachea (EC50) ($10^{-7}$ moles/l) | Compound No. | Number of tests | Potentiating or inhibiting effect of the test substance on the bronchodilating effect of terbutaline |
|---|---|---|---|---|---|---|
|  | H | H (terbutaline, reference) | 2.1 ± 0.5 |  | 6 | — |
| I | CH₃\N—C(=O)—/CH₃ | CH₃\N—C(=O)—/CH₃ | >200 |  | 3 | none |

It is seen in Table 2 that the test substance I did not produce any bronchodilating effect.

No potentiating or inhibiting activity of the test substance I on the bronchodilating effect of terbutaline was observed.

B2. Bronchospasmolytic effect of the test compounds after oral administration in guinea-pigs Test method Male guinea-pigs, Dunkin-Hartley strain, 150–200 g, were used in the study. The animals were starved for about 15 hours (water ad libitum) before the administration, by a stomach tube, of test compound or vehicle (controls). To establish an adequate time period between administration and histamine exposure, the maximum plasma level of terbutaline produced from the hydrolysis of the given pro-drugs of terbutaline was determined. Thus, blood samples (in pre-experimental series) were collected from guinea-pigs at different times after the administration of the test compound and the plasma level of tarbutaline was determined by a massfragmentographic analysis. A peak in the plasma terbutaline was noted 50–60 minutes after the administration, and this time was selected as time for start of histamine exposure.

The histamine aerosol was generated by Bird inline nebulizers from a solution containing 0.02% histamine-HCl and 3% glycerol. The protecting effect was estimated from the delay in appearance of signs of anoxia in drug-treated animals. Of the controls, >90% showed respiratory distress within 3 minutes in the used aerosol. Drug-treated guinea-pigs without any signs of respiratory influence from the histamine during these first 3 minutes were denoted as protected.

Test results

The test results are given in Table 3 below.

TABLE 3

Protecting effect of the test substances against histamine-induced bronchospasm in unanaesthetized guinea-pigs

| Test compound R¹O—/OH/—CH—CH₂—NHC(CH₃)₃ (R²O) | | | Dose protecting 50% of the test animals for more than 3 minutes (ED50) | |
|---|---|---|---|---|
| R¹ | R² | | mg/kg | mmole/kg |
| H | H (terbutaline, reference) | | 0.4 | $1.5 \cdot 10^{-3}$ |
| I CH₃\N—C(=O)—/CH₃ | CH₃\N—C(=O)—/CH₃ | | 2.7 | $6.7 \cdot 10^{-3}$ |

It is seen in Table 3 that the test compound I on molar basis was less potent than the reference substance terbutaline in protecting the test animals against histamine-induced bronchospasm.

C. Effect of the test compounds on isolated heart preparations

C1. In vitro test on isolated guinea-pigs auricles

Test method

Male guinea-pigs strain Dunkin Hartley (400–500 g) were used. After bleeding and removal of the heart the auricles were dissected free from the ventricular part and submerged into carbogen aerated Krebs solution of 37°. The frequency and force of the spontaneously beating preparation was recorded by a Grass transducer FTO3. In the polygraph (Grass 7D) the signals from the isometric transducer passed a trigger function from the drive amplifier to the tachograph to record the rats.

The esterase inhibitor eserine was added to a concentration of $1 \cdot 10^{-6}$ mol/l in the organ bath before the drugs to be tested were added. The intrinsic activity of the test compounds on the heart preparation, that is their effect on heart rate (chronotropic effect) and their effect on the force of the heart beats (inotropic effect), and their possible interaction with terbutaline was studied.

Test results

The test results are given in Table 4 below.

TABLE 4

Effect of the test substances on isolated auricles from guinea-pig heart

Test compound $R^1O$-C$_6$H$_3$(OR$^2$)-CH(OH)-CH$_2$-NH-C(CH$_3$)$_3$

| Compound No. | $R^1$ | $R^2$ | Effect on isolated auricle inotropic effect (relative values) | chronotropic effect (relative values) |
|---|---|---|---|---|
|  | H | H (terbutaline, reference) | 1.0 | 1.0 |
| I | (CH$_3$)$_2$N-C(=O)- | (CH$_3$)$_2$N-C(=O)- | 0 | 0 |

It is seen in Table 4 that the test compound I did not show any chronotropic or inotropic effect.

The possible potentiating or inhibiting response of the test compound I on the chronotropic and inotropic effect of terbutaline was also investigated by adding the test compound to the organ bath in the same concentration as terbutaline. No potentiating or inhibiting effect on the chronotropic and inotropic effect of terbutaline was observed for the test compound I.

C2. In vivo test on the effect of the test compounds on the heart rate in dogs

Test method

Five dogs (Beagle, ♂, 13-18 kg) have been used repeatedly in the study. Each dog was used at most once a week. Food was withheld from the animals the night before the experiment (water ad libitum). The test compound was solved in 8 ml of distilled water, and delivered into the back of the mouth by use of a syringe and a short tube. This oral supply was followed by a water rinse of 8 ml.

The blood was collected from the cephalic veins in the forelegs by use of evacuated tubes. The esterase inhibitor diisopropylfluophosphate (DFP) was added, the samples centrifugated (+5°) and the amount of terbutaline in plasma determined by a massfragmentographic analysis method. The serum level of terbutaline indicates the degree of bronchospasmolytic effect of the test compounds.

The amounts of the test substances to be administered were selected so that the level of terbutaline, when administered per se, corresponds to the serum levels obtained and found effective in patients at clinical use, that is a level of terbutaline of at least 2 ng/ml serum for 6 to 8 hours. The doses of the test substances of the invention were selected so that the serum levels of terbutaline obtained would correspond approximately with the serum levels obtained after administration of terbutaline per se.

The heart rate was determined by a stethoscope (the mean of three determinations during a 5-minute period) before the administration of drug and before each blood sampling.

Test result

The relative effect of the test compounds on the heart rate of the test animals was illustrated by plotting in a diagram the increase in heart rate measured at a certain serum concentration of terbutaline versus the logarithm of the said terbutaline concentration in serum. Only values before and up to the maximal increase in heart rate were used. This method will produce a graph consisting of a substantially straight line. When such a line is drawn for each test compound, it can be seen from the slope of the line how the heart rate is correlated to the serum concentration of the test compound.

In this test, the slope of the line and the coefficient of correlation was investigated for the reference substance terbutaline and for test compound No. I. The results are given in Table 5.

TABLE 5

The influence of the test compounds on the heart rate in dogs

Test compound $R^1O$-C$_6$H$_3$(OR$^2$)-CH(OH)-CH$_2$-NH-C(CH$_3$)$_3$

| Compound No. | $R^1$ | $R^2$ | Tested dosage range (mg/kg) | Slope of the line increase in heart rate vs. logarithm of corresponding serum conc. | Correlation coefficient | Number of measurements |
|---|---|---|---|---|---|---|
| I | H | H (reference) | 0.01-0.1 | 1.04 | 0.9598 | 12 |
|  | (CH$_3$)$_2$N-C(=O)- | (CH$_3$)$_2$N-C(=O)- | 0.3-3 | 0.63 | 0.9324 | 10 |

It is seen in Table 5 that the test compound I produces a relatively much lower increase in heart rate than the reference compound terbutaline.

Comments to the test results from the pharmacological tests

It will first be noted that the compounds of the invention are hydrolyzed in serum and body fluids producing the compound terbutaline, which then exerts its bronchodilating effect. That such a hydrolysis takes place is indirectly obvious from the reported pharmacological tests, where the serum levels etc of terbutaline consistently have been measured.

It is shown in test A that compound I of the invention gives a clinically useful serum level of terbutaline (2 ng/ml serum, or higher) during a time period which is at least twice as long as the time period during which the reference substance terbutaline gives a corresponding serum level (16 hours or more versus 8 hours).

In test B1 (bronchodilating effect in vitro in isolated guinea-pig trachea) it is demonstrated that the test compound I did not exert any intrinsic bronchodilating effect.

No potentiating or inhibiting activity of the test substance I on the bronchodilating effect of terbutaline was observed.

Test B2 demonstrates the bronchospasmolytic effect of the test compound I in vivo test in guinea-pigs. The bronchospasmolytic activity of the test compounds at oral administration was on molar basis about five times less than the activity of the reference compound terbutaline.

In test C1 it is demonstrated in in vitro test that the test compound of the invention per se has no inotropic or chronotropic effect on isolated guinea-pig heart preparation. The esterase inhibitor is added to make sure that it is the intrinsic effect of the test compounds that is measured, and not the effect of the hydrolysis product terbutaline.

Test C2 demonstrates by an in vivo test in dogs that the test compound I of the invention has a considerably reduced stimulating effect on the heart rate compared with the heart rate stimulating effect of terbutaline.

In conclusion, the compounds of the invention ae bronchospasmolytic agents having an exceedingly long duration of action, and they exhibit in addition reduced heart effects compared to the prior art compound terbutaline.

The long duration of activity, measured as the time period during which the serum level of the hydrolysis product terbutaline is at least 2 ng/ml or higher, means that the compounds of the invention will make it possible to reduce the number of times per 24 hours that asthmatic patients have to take their medication. In particular, a duration of therapeutic activity of about 16 hours or more will make it possible to protect the patients effectively and with less side effects during normal periods of sleep with one single dose of the active substance.

What we claim is:

1. A compound of the formula

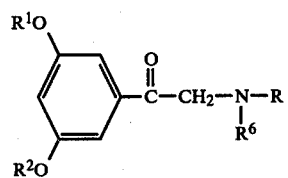

wherein
R is selected from the group consisting of —C(CH$_3$)$_3$,

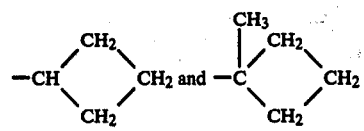

R$^1$ is selected from the group consisting of H and R$^2$,
R$^2$ represents the radical of the formula

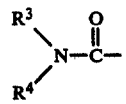

wherein
R$^3$ is selected from the group consisting of
(a) H
(b) alkyl groups containing 1-3 carbon atoms (c) 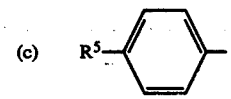

wherein R$^5$ is selected from the group consisting of
(a) OH
(b) alkoxy groups containing 1-3 carbon atoms and
wherein
R$^4$ is selected from the group consistin of
(a) H
(b) alkyl groups containing 1-3 carbon atoms with the proviso that R$^3$ and R$^4$ are combined as follows:

| when R$^3$ is | then R$^4$ is |
| --- | --- |
| H | H |
| alkyl group of 1-3 carbon atoms | H or an alkyl group of 1-3 carbon atoms |
|  | H | wherein R$^6$ is hydrogen or a mono or bicyclic aralkyl group containing not more than 11 carbon atoms.

2. A compound of formula

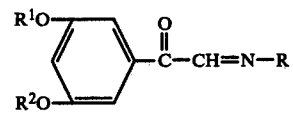

wherein
R is selected from the group consisting of —C(CH$_3$)$_3$,

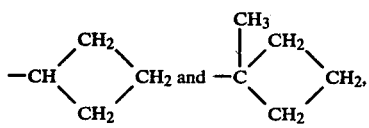

wherein

R$^1$ is selected from the group consisting of H and R$^2$,

R$^2$ represents the radical of the formula

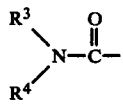

wherein

R$^3$ is selected from the group consisting of
(a) H
(b) alkyl groups containing 1-3 carbon atoms (c) 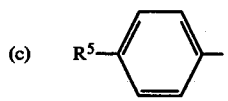

wherein R$^5$ is selected from the group consisting of
(a) OH
(b) alkoxy groups containing 1-3 carbon atoms and wherein R$^4$ is selected from the group consisting of
(a) H
(b) alkyl groups containing 1-3 carbon atoms with the proviso that R$^3$ and R$^4$ are combined as follows:

| when R$^3$ is | then R$^4$ is |
|---|---|
| H | H |
| alkyl group of 1-3 carbon atoms | H or an alkyl group of 1-3 carbon atoms |
| R$^5$—⟨ ⟩— | H |

* * * * *

UNITED STATES PATENT AND TRADEMARK OFFICE
CERTIFICATE OF CORRECTION

PATENT NO. : 4,451,663
DATED : May 29, 1984
INVENTOR(S) : O.A. Torsten Olsson, et al It is certified that error appears in the above-identified patent and that said Letters Patent is hereby corrected as shown below:

On the title page

Page 1 [56] under "References cited" insert --FOREIGN PATENT DOCUMENTS: French Patent 1,324,857--;

Col. 1, line 64, "i.e." should read --i.a.--;

Col. 3, line 26, "with" should start on a new line at the left margin;

Col. 19, line 21, that portion of the formula reading "$R^1$" should read --$R^1O$--;

Col. 20, line 11, "$R^5$" should read --$R^6$--;

Col. 26, line 25, "while" should read --white--;

Col. 32, line 35, "7.58" should read --7.68--.

Col. 32, line 58, "Niglyol" should read --Miglyol--;

Col. 33, line 63, "tert.butylaminoethanse" should read --tert.butylaminoethanol--;

Col. 34, line 62, "(orsiprenaline)" should read --(orciprenaline)--;

Col. 35, line 5, "0.60 g" should read --0.060 g--;

UNITED STATES PATENT AND TRADEMARK OFFICE
CERTIFICATE OF CORRECTION

PATENT NO. : 4,451,663

DATED : May 29, 1984

INVENTOR(S) : O.A. Torsten Olsson, et al

It is certified that error appears in the above-identified patent and that said Letters Patent is hereby corrected as shown below:

Col. 37, under the words "from guinea" in line 1 of Table 2, delete "Compound No.";

Col. 37, line 52, "tarbutaline" should read --terbutaline--;

Col. 38, line 30 insert the heading "Compound No." over the first column of TABLE 3 (reading "I");

Col. 38, line 57, "rats" should read --rate--;

Col. 42, line 39, "with" should start a new line at the left margin;

Col. 44, line 14, "with" should start a new line at the left margin.

Signed and Sealed this

Twentieth Day of November 1984

[SEAL]

Attest:

Attesting Officer

GERALD J. MOSSINGHOFF

Commissioner of Patents and Trademarks